United States Patent [19]
Woo

[11] Patent Number: 5,882,881
[45] Date of Patent: Mar. 16, 1999

[54] INHIBITION OF CYST FORMATION BY CYTOSKELETAL SPECIFIC DRUGS

[75] Inventor: David D. L. Woo, Los Angeles, Calif.

[73] Assignee: The Regents of the University of California, Oakland, Calif.

[21] Appl. No.: 4,804

[22] Filed: Jan. 9, 1998

Related U.S. Application Data

[63] Continuation of Ser. No. 406,910, filed as PCT/US93/09124 Sep. 24, 1993, Pat. No. 5,789,189, and a continuation of Ser. No. 951,270, Sep. 25, 1992, abandoned.

[51] Int. Cl.$^6$ .............................. C12Q 1/24; C12Q 1/02; C12Q 1/10; C12N 5/00
[52] U.S. Cl. ................................ 435/30; 435/29; 435/34; 435/4; 435/41; 435/39; 435/240.2; 435/240.23; 436/63; 514/462; 514/629; 540/478; 549/345
[58] Field of Search ................................ 435/30, 29, 34, 435/4, 41, 39, 240.2, 240.23; 436/63; 514/462, 629; 540/4.78; 549/345

[56] References Cited

U.S. PATENT DOCUMENTS

| | | | |
|---|---|---|---|
| 4,697,600 | 10/1987 | Cardenas et al. | 435/30 |
| 4,814,470 | 3/1989 | Colin et al. | 435/30 |
| 4,853,221 | 8/1989 | Elslager et al. | 435/30 |
| 4,870,162 | 9/1989 | Trovet et al. | 530/350 |
| 4,882,314 | 11/1989 | Takeuchi et al. | 514/352 |
| 4,929,542 | 5/1990 | Risley | 435/30 |
| 4,962,187 | 10/1990 | Pant | 435/30 |
| 4,983,636 | 1/1991 | Takeuchi et al. | 514/352 |
| 5,086,476 | 2/1992 | Bacus | 435/30 |
| 5,124,338 | 6/1992 | King | 514/352 |
| 5,352,805 | 10/1994 | Kingston et al. | 435/29 |
| 5,455,161 | 10/1995 | Assaraf et al. | 435/29 |

OTHER PUBLICATIONS

Wilson, P.; *Cell Biology of Human Autosomal Dominant Polycystic Kidney Disease* 1991. 11(6); pp. 607–616.
Wilson, P. and A. Sherwood, *Tubulocystic Epithelium*, Kidney Int., 1991. 39:pp. 450–463.
Wilson, P.D. *Aberrant epithelial cell growth in autosomal dominant polycystic kidney disease;* Am J. Kidney Dis., 1991. 17(6): pp. 634–637.
Wilson, P.D., et al., *Reversed polarity of Na(+) –K(+) – ATPase: mislocation to apical plasma membrances in polycystic kidney disease epithelia;* Am J. Physiol, 1991. 260: pp. F420–F430.
Gattone, V. and J. Grnatham, *Understanding Human Cystic Desease Through Experimental Models.* Seminars in Nephrology, 1991. 11(^): pp. 617–631.
Gabow, P. and W. Bennet, *Renal Manifestations: Complication Management and Long–Term Outcome of Autosomal Dominant Polysystic Kidney Disease* 1991. 11(6): pp. 643–652.
Grantham, J.J., *Polycystic kidney disease: a predominance of giant nephrons.* Am J. Physiol, 1983. 244(1): pp. F3–F10.
Grantham, J.J., (1988)m *Polycystic kidney desease—an old problem in a new context* {editorial}. N Engl J. Med, 319(14), 944–6.
Grantham, J.J., J.L. Geiser and A.P. Evan, *Cyst formation and growth in autosomal dominant polycystic kidney disease.* Kidney Int., 1987. 31(5): pp. 1145–1152.
Mangoo, K.R. et al., *Ranal epithelial fluid secretion and cyst growth; the role of cyclic AMP.* Faseb J, 1989, 3(14): pp. 2629–2932.
Avner, E.D., et al., *Congenital murine polycystic kidney disease. I. The ontogeny of tubular cyst formation.* Pediatr Nephrol, 1987. 1(4): pp. 587–596.

(List continued on next page.)

*Primary Examiner*—Louise N. Leary
*Attorney, Agent, or Firm*—Knobbe, Martens, Olsen & Bear LLP

[57] ABSTRACT

The invention provides a method of producing a culture of polycystic kidney cells which form cysts in vitro. A cell culture of polycystic kidney cells is also provided. A method for screening an agent in vitro to determine the effectiveness of the agent in treating polycystic kidney disease is disclosed. Further, a method of treating a mammal having polycystic kidney disease by administering a pharmaceutical composition is provided.

30 Claims, 5 Drawing Sheets

OTHER PUBLICATIONS

Avner, E.D., et al. "Sodium–potassium ATPase activity mediates cyst formation in metanephric organ culture"; Kidney Int., 1985. 28(3): pp. 447–455.

Avner, E.D., et al. "Congenital murine polycystic kidney disease"; II. Pathogenesis of tubular cyst formation. Pediatr Nephrol. 1988. 2(2): pp. 210–218.

Wani, M. and et al., *"Plant antitumor agents. VI. The isolation and structure of taxol, a novel antileukemic and antitumor agent from Taxus brevifolia"*; J. Am. Chem. Soc. 1971. 93: pp. 2325–2327.

Schiff, P., J. Fant, and S. Horwitz, *Promotion of microtubule assembly in virto by taxol.* Nature, 1979, vol. 277, pp. 665–667.

Schiff, P. and S. Horwitz, *Taxol Stabilizes microtubules in mouse fibroblast cells.* Proc. Nat. Acad. Sci. 1980. 77: pp. 1561–1565.

Neufeld, T.K., et al., J.J. Kidney Int. 41: 1222–1236 (1992). *In vitro formation and expansion of cysts derived from human renal cortex epithelial cells.*

K.D. Gardner, in *The Cystic Kidney,* K.D. Gardner, J. Bernstein, Eds. (Kluwer Academic Publishers, Hingham, MA, 1990). pp. 3–17; "Cysts and Cystic Kidneys".

E. Levine, J.J. Grantham, in *The Cystic Kidney,* K.D. Gardner, J. Bernstein, Eds. (Kluwer Academic Publishers, Hingman, MA, 1990) pp. 171–206, "Radiology of Cystic Kidneys".

W.J. Kimberling, et al., *N. Engl. J. Med.* 319, 913–917 (1988); "Linkage Heterogeneity of Autosomal Dominant Polycystic Kidney Disease".

L. Bachner, et al., *Hum Genet* 85 221–217 (1990); "Linkage study of a large family with autosomal dominant polycystic kidney disease with reduced expression".

G. Romeo, et al., *Lancet,* 2, 8–10 (1988); "A Second Genetic Locus For Autosomal Dominant Polycystic Kidney Disease".

S. Norby, W.W.S. Sorensen, P. Boesen, In *Genetics of Kidney Disorders.* (1989), vol. 305, pp. 83–88; "Non–Allelic Genetic Heterogeneity of Autosomal Dominant Polycystic Kidney Disease?".

S.T. Reeders, et al., *Nature* 317, 542–4 (1985); "A highly polymorphic DNA marker linked to adult polycystic kidney disease on chromosome 16".

S.T. Reeders, et al., *Lancet* 8497, 6–8 (1986); "Prenatal Diagnosis of Autosomal Dominant Polycystic Kidney Disease with a DNA Probe".

P.D. Wilson, R.W. Schrier, R.D. Breckon, P.A. Gabow, *Kidney Int.* 30, 371–378 (1986); "A new method for studying human polycystic kidney disease epithelia in culture".

A.H. Yang, K.H. Gould, T.D., Oberley, *In Vitro Cell Dev Biol* 23, 34–46 (1987); "In vitro growth and differentiation of Human Kidney Tubular Cells on a Basement Membrane Substrate".

F.A. Carone, S. Nakamura, B.S. Schumacher, P. Punyarit, K.D. Bauer, *Kidney Int.* 35, 1351–1357 (1989); "Cyst–derived cells do not exhibit accelerated growth or features of transformed cells in vitro".

J.D. Valentich, R. Tchao, J. Leighton, *J. Cell Physio* 100, 291–304 (1979); "Hemicyst Formation Stimulated by Cyclic AMP in Dog Kidney Cell Line MDCK".

T.P. Fleming, M.H. Johnson, *Annu Rev Cell Bio* 4, 459–85 (1988); "From Egg to Epithelium".

F.E. Cuppage, R.A. Huseman, A. Chapman, J.J. Grantham, *Kidney Int.* 17, 372–81 (1980); "Ultrastructure and Function of Cysts from Human Adult Polycystic Kidneys".

S.K. Katz, A. Hakki, A.S. Miller, F.S.D., Ann. Clin. Lab.Sci. 19, 352–359 (1989); "Ultrastructural Tubular Basement Membrane Lesions in Adult Polycystic Kidney Disease".

I. Ebihara, et al., Lab. Invest, 58, 262–269 (1988); "Altered mRNA Expression of Basement Membrane Components in a Murine Model of Polycystic Kidney Disease".

M. Taub, G.W. Laurie, G.R. Martin, H.K. Kelinman, Kidney Int. 37, 1090–1097 (1990); "Altered basement membrane protein biosynthesis by primary cultures of cpk/cpk mouse kidney".

Y.S. Kanwar, F.A. Carone, *Kidney Int* 26, 35–43 (1984); "Reversible changes of tubular cell and basement membrane in drug–induced renal cystic disease".

F.A. Carone, *Semin Nephrol* 8, 89–93 (1988); "Functional Changes in Polycystic Kidney Disease are Tubulo–Interstitial in Origin".

J.J. Grantham, *Am J Kidney Dis* 15, 110–6 (1990); "Polycystic Kidney Disease: Neoplasia In Disguise".

G.M. Edelman, *A Rev. Cell Biol.* 2, 81–116 (1986); "Cell Adhesion Molecule in the Regulation of Animal Form and Tissue Pattern".

G.R. Martin, R. Timple, *A. Rev. Cell Biol.* 3, 57–85 (1987); "Laminin and Other Basement Membrane Components".

M. Takeichi, Development 102. (1988), pp. 639–655; "The cadherins: cell–cell adhesion molecules controlling animal morphogenesis".

P. Ekblom, D. Vestweber, R. Kemler, *A. Rev.Cell Biol.* 2, 27–47 (1986); "Cell–Matrix Interactions and Cell Adhesion During Development".

J.B. De Almeida, J.L. Stow, Am. J. Physiol. 260, C691–C700 (1991); "Disruption of microtubules alters polarity of basement membrane proteoglycan secretion in epithelial cells".

M.J. Rindler, I.E. Ivanov, D.D. Sabatini, *J Cell Biol,* 104, 231–241 (1987); "Microtubule–acting Drugs Lead to the Nonpolarized Delivery of the Influenza Hemagglutinin to the Cell Surface of Polarized Madin–Darby Canine Kidney Cells".

R.B. Kelley, Cell 61, 5–7 (1990); "Microtubules, Membrane Traffic, and Cell Organization".

B.R. Stevenson, J.D. M. Siliciano M.S., D.A. Goodenough, *J.Cell Biol.* 103, 755–766 (1986); "Identification of ZO–1: A High Molecular Weight Polypeptide Associated with the Tight Junction (Zonula Occludens) in a Variety of Epithelia".

I. Meza, G. Ibarra, M. Sabanero, A. Martinez–Palomo, M. Cereijido, *J Cell Bio* 87, 746–754 (1980); "Occluding Junctions and Cytoskeletal Components in a Cultured Transporting Epithelium".

B. Gumbiner, B. Stevenson, A. Grimaldi, *J Cell Biol* 107, 1575–87 (1988); "The Role of the Cell Adhesion Molecule Uvomorulin in the Formation and Maintenance of the Epithelial Junctional Complex".

S. Horikoshi, S. Kubota, M. G. R., Y. Yamada, K. P.E., Kidney Int. 39, 57–62 (1991); "Epidermal growth factor (EGF) expression in the congenital polycystic mouse kidney".

B.D.J. Cowley, F.L.J. Smardo, J.J. Grantham, J.P. Calvet, *Proc Natl Acad Sci USA* 84, 8394–8 (1987); "Elevated c–myc protooncogene expression in autosomal recessive polycystic kidney disease".

V.H. 2, Gattone, et al., *Dev Biol* 138, 225–30 (1990); "Defective Epidermal Growth Factor Gene Expression in Mice with Polycystic Kidney Disease".

Physician's Desk Reference, 1992, Velban, p. 1273.

Physician's Desk Reference, 1992, Benemid, p. 1388.

Physician's Desk Reference, 1992, Oncovin, p. 1256.

Physician's Desk Reference, 1992, Colchicine, p. 1221.

Nephrol Dial Transplant (1992);7:545–557; *Abstracts of the Renal Association and British Association of Paediatric Nephrology,* Royal College of Physicians, London, UK, 28–29 Oct. 1991.

The American Society of Nephrology; Nov. 19, 1992; Annual Meeting and Exposition; David Woo; *Cytoskeletal Specific Drugs Inhibit In–Vitro Cyst Formation;* and *Taxol Prolonged Survival of C57BL/6–cpk/cpk (CPK) Mice.*

J. Am. Soc. Nephrol. 2(3) (1991) p. 261, Sep. 25, 1991; "Spontaneous in Vitro Cyst Formation: A Novel Model from the Polycystic cpk/cpk Mouse (CPKM) Kidney".

Woo; Journal of American Society of Nephrology; vol. 3, No. 3, 1992; p. 302; *Cytoskeletal specific drugs inhibit in–vitro cyst formation.*

Ravia, et al.; Human Genetics; vol. 71, No. 4, 1985; pp. 294–300; *Differences between cystic fibrosis and normal cells in the degree of satelite association.*

Forrest; Biochemical and Biophysical Research Communications; vol. 98, No. 1; Jan. 15, 1981; pp. 324–329; *Colchicine Binding activity and Tyrosyl tubulin ligase activity in normal and cystic fibrosis fibroblasts.*

Siegal, et al.; Transplantation; vol. 54, No. 3; 1992; p. 1131; *The polycystic kidney donor.*

Merck & Co.; Budavari, S.Ed.: *The Merck Index;* 1989; p. 1435.

Rubino et al., Europ. J. Cell Biology, vol. 30, pp. 182–190 (1983).

INHIBITION OF CYST FORMATION BY CYTOSKELETAL SPECIFIC DRUGS

This application is a continuation of prior application Ser. No. 08/406,910 filed May 22, 1995, now U.S. Pat. No. 5,789,189, which is a Section 371 application of International Application No. PCT/US93/09124 filed on Sep. 24, 1993, and a continuation in part of Ser. No. 07/951,270 filed Sep. 25, 1992.

STATEMENT OF UNITED STATES GOVERNMENT SUPPORT

Certain aspects of this invention were made with United States government funding under NIH Grant No. DK 40700. The United States government has certain rights in these aspects of the invention in the United States.

FIELD OF THE INVENTION

The present invention relates to cystic diseases. More specifically, the invention relates to the use of a culture of cells that form cysts in vitro, to a method of screening for agents which can treat such diseases, and to pharmacological treatments of the diseases.

BACKGROUND OF THE INVENTION

Cytoskeletal Components of the Cell

The cytoskeleton plays an important role in the growth, division, and migration of eukaryotic cells. Changes in cellular morphology, the repositioning of internal organelles, and cellular migration all depend on complex networks of protein filaments that traverse the cytoplasm.

These protein filaments fall into three main categories according to their size: microtubules, intermediate filaments, and microfilaments. Both microtubules and microfilaments are made of globular subunits which can quickly polymerize and depolymerize in the cell resulting in movement and morphological changes. Intermediate filaments are made of fibrous protein subunits and tend to be more stable with longer half-lives than most microtubules and microfilaments.

Current theory holds that cells have a pool of unpolymerized globular subunits in the cytoplasm which is used to rapidly form the cytoskeletal microtubules and microfilaments. Microtubules are formed by a dimer of tubulin proteins which take on a helical shape to form filaments. Similarly, microfilaments comprise actin proteins which agglutinate together to form elongated filaments. In addition to these fibers, the cytoskeleton is also made up of many other components for linking the filaments to each other or to the plasma membrane. Many cytoplasmic components can influence the rate of filament polymerization or depolymerization. Also, drugs have been discovered which affect the rate of filament polymerization and lead to either abnormal accumulations of protein filaments or unpolymerized globular subunits.

Taxol, colchicine, vinblastine, cytochalasin-B, and cytochalasin-D are all well known disruptors of cytoskeletal development. Taxol inhibits depolymerization of the microtubule filaments, while vinblastine and colchicine inhibit microtubule polymerization. Griseofulvin is another drug that interferes with microtubule function, although the mechanism of this interference is not yet established. Cytochalasin-B and cytochalasin-D are inhibitors of microfilament networks.

Diseases Involving Cyst Formation

There are many human diseases which result in the formation of cysts which contain either semi-solid or fluid material. The contents of a cyst sometimes derive from normally retained fluid (e.g. a sebaceous cyst can contain fluid from a blocked sebaceous gland) or from a parasitic infection. Benign cysts can occur in the ovary, spleen, lungs, kidney and liver, where they are often congenital. Some congenital cysts result from fetal malformations and developmental failure while others are direct results of a disease state.

The polycystic kidney diseases (PKD) are a group of disorders characterized by a large number of cysts distributed throughout dramatically enlarged kidneys. The resultant cyst development leads to impairment of kidney function and can eventually cause kidney failure. In humans, PKD can be inherited in autosomal dominant (ADPKD) or autosomal recessive (ARPKD) forms.

ADPKD is the most common dominantly inherited kidney disease of humans, while ARPKD occurs relatively rarely. Clinically, ADPKD represents a major cause of chronic renal failure in humans and accounts for 10% of all patients requiring chronic dialysis or renal transplantation. Currently, 500,000 Americans and 5 million people worldwide are estimated to be afflicted with PKD. In the U.S. this represents an annual health care cost of nearly one billion dollars.

PKD probably begins in utero in most patients with the kidneys increasing in size and ultimately showing signs of disease in the fourth or fifth decade of life. At present there are methods of detecting PKD in utero. Approximately 25% of patients do not have a family history consistent with ADPKD, suggesting either that the genes responsible have a high mutation rate or that other environmental factors are at work.

Even though the specific gene defect responsible for PKD is unknown, the most common locus found by linkage studies is found on human chromosome 16p. Both in vivo and in vitro studies of ADPKD kidneys have suggested that a variety of disease manifestations (including accelerated renal epithelial cell growth, basement membrane abnormalities and mislocalized membrane proteins) are potentially important in the etiology and maintenance of renal cysts. Additional cysts involving the liver or spleen, and brain aneurysms, have been found to be present in about ten percent of ADPKD patients suggesting that the disorder affects organs other than the kidneys.

To discover the molecular basis for cyst formation relating to PKD, researchers have employed both in vitro and animal models. Previous in vivo and organ culture studies have implicated both accelerated renal epithelial cell growth and electrolyte transport abnormalities in the genesis of these cysts.

Monolayer cultures of both normal and polycystic human kidneys have similar limited life spans and can be passaged using either serum free or supplemented media. Virtually no cysts or hemicysts have ever been observed in these cultures. In contrast, MDCK and LLCPK are two immortalized normal renal cell lines that spontaneously form hemicysts and cysts in culture. Cyst formation has also been reported in cultures of normal human thyroid, mammary and lung cells. Normal and polycystic kidney epithelial cells, embedded in collagen can be induced to form cysts when stimulated with serum, forskolin, or epidermal growth factor. However, conditions enabling the differential expression of normal and polycystic kidney phenotypes using disbursed cells in culture has not been achieved.

In vivo experiments have been performed on a mouse strain (CPK) which is homozygous for a gene that causes a murine polycystic kidney disease. This murine model arose as a spontaneous mutation of the C57BL/6J strain housed at the Jackson laboratories, and newborn pups rapidly develop a severe form of polycystic kidney disease. Numerous proximal cysts are found in the kidney cortex of these CPK mice at birth.

These proximal cysts progressively enlarge and by day 10 the collecting duct segments of thousands of kidney tubules begin to dilate and develop into large fluid filled cysts throughout the kidney medulla. Impairments of renal functions parallel the enlargement of these collecting duct cysts. Affected mice become visibly lethargic due to azotemia around day 20–25 after birth and usually die of uremia and kidney failure before the 28th day.

Mechanistically, three types of abnormalities in normal kidney tubules have been implicated in the genesis and progression of cysts in PKD: (1) renal tubules begin to enlarge, forming a cyst, (2) additional cells line the nephron wall, and (3) a net change in renal fluid handling occurs allowing fluid to accumulate inside the cyst cavity.

Each of these three steps can be coded for by the same or different polycystic kidney disease genes. However, it is still unknown whether these observed phenomena are the direct result or secondary manifestation of altered genes in PKD. It is known that cysts arise from the progressive focal dilation of preexisting kidney tubules. Unfortunately, except for dialysis and transplantation, which are palliative, no curative treatment exists for PKD. A curative treatment for cystic disease, especially PKD, would therefore present an important medical breakthrough.

SUMMARY OF THE INVENTION

The present invention provides methods of producing cell cultures which form cysts in vitro, methods of using such cell cultures to screen for agents or compounds that have anti-cystic activity, and methods of treating subjects who have a cyst or who have a disease which causes cysts. In particular, kidney cells from a human afflicted with a polycystic kidney disease, such as Autosomal Dominant Polycystic Kidney Disease, can be made to form cysts in vitro, and such cells can be cultured in the presence of an agent or compound which has anti-cystic activity. Once such a compound has been identified, it can be used to treat a cyst or cystic disease.

One of the surprising discoveries of the present invention is that agents which affect the proper functioning of the cytoskeleton or which affect the transport of membrane proteins to the cell membrane can be used to treat cysts and cystic diseases. Such agents include compounds which depolymerize microtubules, such as colchicine, vinblastine, vincristine, and nocodazole, as well as compounds which stabilize microtubule structures, such as taxol and derivatives thereof. Also included in the list of compounds which can be used to treat cysts and cystic disease are compounds which depolymerize actin microfilaments, such as cytochalasin B and cytochalasin D, those which stabilize actin microfilaments, such as phalloidin, and some, such as griseofulvin, which interfere with microtubule function by an unknown mechanism.

In one aspect, the present invention comprises a method of producing a culture of cells which form cysts in vitro by forming a suspension of cells that form cysts in vivo in a medium suitable for their maintenance. By culturing such cells on a solid phase which substantially prevents the formation of a layer of these cells on the surface of the solid phase, the cells form cysts in vitro. In one embodiment, the solid phase is coated with a material such as agarose that prevents cells from forming a monolayer on the surface of the solid phase. One particular embodiment involves the culturing of cells from a subject with a polycystic kidney disease on an agarose coated solid phase, wherein the apical surfaces of the in vitro cysts formed by such cells face the lumens of these cysts.

In another aspect of the present invention, a method is provided in which cells that form cysts in vivo are also cultured in vitro on a solid phase without the formation of a layer of such cells on the surface of the solid phase. However, in this method, these cells are cultured in a medium comprising an agent or compound to be tested for its ability to inhibit cyst formation. By detecting the extent to which the cells form cysts in culture, the effectiveness of the agent or compound in treating cysts or cystic diseases can be determined.

In a further aspect of the-present invention, a method of treating a mammal having a cyst or a cystic disease is disclosed. In the inventive method, a mammal having a cyst or cystic disease is first identified. In the case of a human, such identification could be by being diagnosed by a physician. After identifying such a mammal, a pharmacologically effective anti-cystic amount of an agent or compound that interferes with the normal metabolism or functioning of a cytoskeletal component is administered to the mammal in a pharmacologically acceptable carrier. For example, the compound can be one that specifically binds to microtubules or to actin and which either causes the depolymerization of these components or which prevents such depolymerization.

In yet another aspect of the present invention, another method of treating a mammal having a cyst or a cystic disease is provided. In this method, a mammal having a cyst or a cystic disease is again identified, after which a pharmacologically effective anti-cystic amount of a compound that inhibits the delivery of membrane proteins to the membrane of a cell of the mammal is administered in a pharmacologically acceptable carrier. For example, the compound brefeldin A can be used to treat such a mammal.

The present invention also includes the use of an agent that interferes with the normal functioning of a cytoskeletal component or an agent that inhibits the delivery of membrane proteins to the membrane of a cell in the manufacture of a medicament for the treatment of a mammal having a cystic disease. Such an agent can comprise, for example, any of the previously mentioned agents that interfere with the functioning of a cytoskeletal component or with the delivery of membrane proteins to cell membranes.

Further aspects of the present invention will become apparent to those of ordinary skill in the art upon reference to the ensuing detailed description of the invention.

DESCRIPTION OF THE FIGURES

FIG. 1 shows $^3$H-dThd incorporation in cultures of normal and CPK kidneys. Hollow bars designate normal littermates and solid bars are CPK. Panels (a) and (b) show $^3$H-dThd incorporation in suspension cultures in (a) serum-free and (b) serum supplemented media. Panels (c) and (d) show $^3$H-dThd incorporation in monolayer cultures in serum-free and supplemented media, respectively. Data are mean ±SD, n=3 wells for each time-point from cells derived from day 10, 21 and 28 postnatal kidneys. $^3$H-dThd is given as cpm/µg protein. * indicates p<0.05 between normal and CPK cells at each time point.

FIG. 3 shows the effects of taxol or methotrexate treatment on the growth and survival of heterozygous and cpk mice. The body weights of untreated, taxol treated and methotrexate treated C57BL/6j mice between day 10 and day 45 after birth is shown in A. The body weights of untreated, taxol treated and methotrexate treated cpk mice are shown in B. Results in each group are the mean of 6 animals. Untreated and methotrexate treated cpk mice died between days 26 and 28. Taxol treated cpk mice live for an average of 45±2 days.

DETAILED DESCRIPTION OF THE INVENTION

I have discovered that cystic diseases can be treated pharmacologically in mammals using compounds that affect the cytoskeleton of mammalian epithelial cells. Included among the compounds that are effective inhibitors of cyst formation are those that interfere with the normal metabolism or function of a cytoskeletal component. Other compounds I have found to have pharmacologically effective anti-cystic activity include those that inhibit the delivery of membrane proteins to the membranes of cyst-forming cells.

I have also developed an in vitro assay system in which my initial discoveries were made. This assay system serves as a basis for identifying additional agents that can inhibit cyst formation within the context of the present invention.

Development of the In vitro Assay System

As discussed above, my initial discoveries of compounds effective in the inhibition of cyst formation were made using an exemplary in vitro assay system. This exemplary system has been produced using both cultured human polycystic kidney (ADPKD) cells and cultured murine (CPK) cells. However, as discussed in greater detail below, there are a variety of other cells able to form cysts in vivo that can also be used. It is known that monolayer cultures of both normal and polycystic human kidneys can be cultured in vitro. However, under ordinary conditions, virtually no cysts or hemicysts can be observed in these cultures. See, e.g. J. D. Valentich, R. Tchao, J. Leighton, *J Cell Physiol* 100:291–304 (1979). Both normal and polycystic human kidney epithelial cells can be induced to produce cysts if embedded in type 1 collagen and stimulated with serum, forskolin or epidermal growth factor. See, e.g. Mangoo-Karim R, Uchic M E, Grant M, Shumate W A, Calvert J P, Park C H and Grantham J J, *The FASEB Journal* 3:2629–2632 (1989); and Neufeld T K, Douglass D, Grant M, Ye M, Silva F, Nadascy T and Grantham J J *Kidney Int.* 41:1222–1236, 1992. Unfortunately, such induced cyst formation does not differentiate between normal cells and cells that will develop into cysts. Thus, such a system is not believed to serve as a good in vitro model for cystic disease.

My exemplary in vitro system provides conditions that enable the differential expression of normal and polycystic phenotypes using dispersed cells in culture. Such a system has not, to my knowledge, heretofore been achieved. The exemplary in vitro system of the present invention provides cells that have the unique ability to develop into cysts in unstirred suspension culture. The process of cyst formation in this system closely mimics the formation of the blastocoele cavity in blastocysts, as reported by T. P. Fleming et al. in *Ann. Rev. Cell Biol.* 4:459–85 (1988).

In my in vitro assay system, a suspension of cells that can produce cysts in vivo is first formed in a medium in which the cells will grow. Suitable cells include ovarian cyst cells, breast cyst cells, bronchogenic cyst cells, choledochal cyst cells, colloidal cyst cells, congenital cyst cells, dental cyst cells, epidermoid inclusions, hepatic cyst cells, hydatid cyst cells, lung cyst cells, mediastinal cyst cells, ovarian cyst cells, periapical cyst cells, pericardial cyst cells, in addition to the polycystic kidney disease cells, such as human ADPKD cells or murine CPK cells discussed above. The cells are then cultured on a solid phase without formation of a layer of the cells thereon. In one embodiment, the solid phase is coated with a material that will not allow the cells to form a layer in any substantial amount. I have discovered that an agarose coating is one material effective in preventing cell layer formation.

One example of an in vitro assay system for cyst-formation is provided below as Example 1. As such, this Example, like all Examples provided herein, is provided merely to illustrate certain aspects of the present invention, and not to limit the invention in any way.

EXAMPLE 1

In vitro Cell Culture System

At 10, 21 and 28 days after birth, mice having congenital polycystic kidney disease (CPK) and their phenotypically normal littermates were sacrificed by cervical dislocation. Kidneys were harvested aseptically and washed with DMEM/F12 (Sigma Chemical Co., St. Louis, Mo.) in a 1:1 mix. Each decapsulated kidney was chopped into cubes (1 mm) and incubated in 5 ml of collagenase solution composed of 1 mg/ml collagenase type IV (Worthington Biochemical Corporation, Freehold, N.J.), 1 mg/ml egg white trypsin inhibitor (Worthington) in 1:1 DMEM/F12.

For experiments in which renal collecting tubular cells from normal kidneys were assayed for their ability to form cysts in vitro, kidneys were cut into halves and the medulla dissected out to provide tissues for harvesting cells. Tissue samples were then incubated at 39° C. for 2–3 hrs and the mixture was shaken vigorously at 15–30 minute intervals to promote dissociation. Next, the preparation was centrifuged at 200×g for 1 minute and the supernatant discarded. The pellets were resuspended in 14 mls 1:1 DMEM/F12 with or without 10% calf serum (Irvine Scientific, Santa Ana, Calif.), and larger aggregates were removed by allowing them to settle under gravity for 2 minutes.

The top 12 mls, which contained both single cells and aggregates of up to 10 cells, as assessed by inverted phase-ontrast microscopy, were placed in 2 ml aliquots in the wells of plastic culture plates (Corning, N.Y.) precoated with 1% agarose in DMEM:F12 (2 ml in each well of a 6-well plate; 1 ml in each well of a 24-well plate). Cell samples were digested with further incubation for 10 minutes in 0.05% trypsin and 0.53 mM EDTA (Gibco, BRL Gaithesburg, Md.) at 37° C. All cultures were plated at a final density of $1-3\times10^4$ cell, per well. For growth studies of monolayer cells, identical preparations were grown on the plastic surface of the culture plates. Both the monolayers and the cell suspensions were incubated at 37° C. in a moisture saturated incubator in 5% $CO_2$ and air.

I have substituted human ADPKD cells for the murine CPK cells of Example 1 and produced similar results. Other cyst-forming cells are believed to also form suitable results with only minor deviations from the conditions set forth in Example 1.

In the murine system of Example 1, cysts form in both serum-free and serum-containing medium with similar efficiencies and can be maintained in culture for at least six weeks. When viewed with the aid of a light microscope, cells from normal C57BL/6J mouse kidneys were observed to form aggregates of 10–50 cells. However, no cysts could be observed by 24 hours of culture, or during a prolonged culture to 72 hours. In contrast, kidney cell suspensions from all the studied ages of CPK mice had formed both aggregates and cysts by 24 hours of culture. These cysts exhibit a characteristic spheroid shape roughly 50–100 microns in diameter when viewed with the light microscope. The range of cyst size was similar in all age groups but became progressively more frequent, when expressed as cyst frequency per total cell number at 24 hours of culture, in 10, 21 and 28 day old CPK mice. Table I shows cyst diameter as mean±Standard Deviation (SD) for 20 mice at each age. Cyst frequency (n=2, each age) is expressed as % of number of cysts in cultures from day 28 CPK mice after factoring for total cell number in suspension.

TABLE I

Cyst diameter and frequency at 24 hours
of suspension culture in serum-free media

| Age of CPK mouse (days) | Cyst Diameter ($\mu$m) | Cyst Frequency (% of day 28) |
| --- | --- | --- |
| 10 | 69 ± 12 | 29 |
| 21 | 71 ± 22 | 42 |
| 28 | 58 ± 25 | 100 |

Using phase-contrast microscopy on cpk cells, and serial three-hour observations, lumens could first be identified at six hours after the initiation of culture while continuing to enlarge during the subsequent 18 hours of observation. There was no difference in cyst size or frequency in either serum-free or supplemented media samples. If cells were treated with trypsin after collagenase, cell aggregates formed in both CPK and normal mice, but lumen formation was not observed. Since mature CPK cysts are predominantly found in collecting ducts in vivo, the possibility exists that in vitro cyst formation can be a result of the enrichment of collecting duct cells in polycystic CPK kidneys. However, virtually no cysts were observed in three experiments where preparations enriched in collecting duct cells prepared from the kidney medulla of normal mouse kidneys were used in the in vitro cyst formation assay system.

I further analyzed the growth of cells in this culture system using a variety of techniques. Sample techniques used in this analysis are shown below in Example 2.

EXAMPLE 2

Growth Studies of Murine Cysts

Growth studies were performed on kidney cells derived from day 10, 21 and 28 postnatal CPK mice and their normal littermates. Immediately after cells were placed in suspension or monolayer culture, 3 $\mu$Ci of $^3$H-thymidine ($^3$H-dThd, specific activity 45 Ci/mmol, Amersham, Ill.) was placed in each well of the culture plate. DNA synthesis was assessed by incorporation of $^3$H-dThd over the 24 hours of culture, and trichloroacetic acid-insoluble. radioactivity was expressed as cpm/$\mu$g protein. Protein was assayed with the BCA reagent as described by the manufacturer (Pierce, Rockford, Ill.). At 24 hours of culture, an aliquot (0.2 ml) of the suspension was removed and the number of cysts counted using an inverted microscope. The number of cysts was expressed as a ratio factored for the total number of cells in the suspension at 24 hours of culture. Cyst diameter was measured at 100× using an eyepiece micrometer.

FIG. 1 shows the incorporation of $^3$H-dThd recorded over the first 24 hours of culture in cells derived from day 10, 21 and 28 postnatal kidneys after treatment as in Example 2. This provides an indication of DNA synthesis in these cells. The hollow bars designate normal littermates and solid bars are CPK. Panels (a) and (b) show $^3$H-dThd incorporation in suspension cultures in (a) serum-free and (b) serum supplemented media. Panels (c) and (d) show $^3$H-dThd incorporation in monolayer culture in serum-free and supplemented media, respectively. The data shown in FIG. 1 are mean ±SD, with three wells for each time-point from cells derived from day 10, 21, and 28 postnatal kidneys. The incorporation of $^3$H-dThd into macromolecules is given as cpm/$\mu$g protein. The * indicates p<0.05 between normal and CPK cells at each indicated time point.

In both suspension and monolayer cultures of normal kidney cells, $^3$H-dThd incorporation was maximal in cells harvested from day 10 kidneys, and fell sequentially in cultures from 21 and 28 day old mice. Incorporation was higher in serum-supplemented versus serum-free media; however, in cells from day 10 CPK kidneys, $^3$H-dThd incorporation was similar to normal littermates under all culture conditions. In marked contrast to cultures of normal cells, $^3$H-dThd incorporation in both monolayer and suspension cultures of day 21 and 28 CPK kidney cells was maintained at values the same as day 10 CPK cells. As a result, the mean values for day 28 CPK cells were significantly higher than those of kidney cells from normal littermates.

Both normal and polycystic cells generated in the culture system of Example 1 were further examined through a variety of techniques. Example 3 shows a micropuncture technique for further analysis of the cysts formed in the in vitro assay system described herein.

EXAMPLE 3

Micropuncture Technique

In vitro cysts derived from 21 day old CPK mice were subjected to micropuncture. Intracystic hydrostatic pressure was measured in random cysts suspended in culture medium after 24 hours of incubation. The measurement was directly obtained by a servonulling pressure sensor (Instrumentation for Physiology and Medicine, San Diego, Calif.) employing a 1 $\mu$m tip diameter glass pipette filled with hypertonic saline (1.2M). The intraluminal hydrostatic pressure from the servonull system was monitored with an electronic pressure transducer (model P23 Gb) and was recorded on a Gould amplifier chart recorder.

When intraluminal hydrostatic pressures within six cysts formed in the system of Example 1 were analyzed by micropuncture, pressures of 1.2–3.0 mmHg, with a median of 2.0 mmHg were recorded. However, in human cells steady state, intraluminal hydrostatic pressures of up to 10 mm of mercury have been measured. The cysts collapsed upon puncture and the recorded pressure returned to baseline within one minute. In contrast, attempted punctures of cell aggregates did not result in a pressure deviation from baseline.

The cysts were also analyzed by light and electron microscopy. Procedures for such techniques are provided in Example 4.

EXAMPLE 4

Microscopy of Cysts

In vitro cysts derived from day 21 CPK mice were processed for light and transmission electron microscopy. Each gram of kidney tissue from either normal (n=9) or polycystic human kidneys (n=10) were trimmed into 1–3 mm cubes and dispersed into single cells with 10 mls of 0.22 micron filter sterilized type IV collagenase (Worthington, Freehold, N.J.) dissolved at 1 mg/ml in DMEM/F12 for 3 hrs at 37° C. with vigorous shaking at 15 minute intervals to promote tissue dissociation.

Cell suspensions were separated from debris by sedimentation at unit gravity and decantation. After washing once with DMEM/F12 medium, cells were suspended in DMEM/F12 supplemented with 1.2 gm/l sodium bicarbonate, 1× insulin, transferrin and selenium (Sigma # 11184), 1% lipids supplement (Sigma # L4646) and 1× antibiotic/antimycotic (Sigma # A7292) at a density of $5 \times 10^4$ cells per ml. Two mls of the cell suspension were aliquoted into each well of a six-well plastic cell culture plates that had been precoated with 2 mls of 1% low melting point agarose in DMEM/F12 and incubated at 37° C. in a humidified atmosphere of 5% $CO_2$ in air.

The agarose coating prevented cells from adhering to the plastic substrate. In addition, cells do not attach to agarose and are maintained as a stationary suspension. Typically, 100 to 150 cysts can be prepared from one gram of polycystic kidney tissue.

Cyst cells were fixed in 1% paraformaldehyde (Sigma Chemical Co.) and 0.5% glutaraldehyde (Sigma) in phosphate buffered saline (pH 7.2), post-fixed with 1% osmium tetroxide, dehydrated through graded ethanols and embedded in medcast resin (Ted Pella, Inc. Redding, Calif.). Semi-thin sections (1 $\mu$m) were stained with toluidine blue for light microscopy and thin sections (50 nm) stained with saturated uranyl acetate and Reynold's Lead citrate and examined in a Philips 300 electron microscope.

When viewed in cross-section under the light microscope, the cysts formed in the human ADPKD in vitro system can be seen to have an outer layer one cell thick. These cysts range from 10–50 cells in circumference. Some of the cysts that have been viewed under the scanning electron microscope have a deflated appearance that suggests the structure is hollow rather than a solid aggregate of cells. Such balls of cells can be estimated to be roughly 100 microns in diameter. Interestingly, other scanning electron micrographs reveal cysts having sphere-like structures where a portion of the cell layer has detached. In such cysts, a basement membrane layer can be clearly seen. Transmission electron microscopy demonstrated the presence of short, sparse microvilli on the anti-lumenal surfaces of the cells that lined the walls of these cysts.

Transmission electron microscopy reveals that the cells lining the cysts are polarized. These cells have apical tight junctions between adjacent cells and have an abnormally thickened basement membrane on the basal surface. This basement membrane, which is estimated to be roughly 0.5 microns thick, faces the lumen of the cyst and bears a striking morphological resemblance to the basement membrane lining "proximal" cysts in human ADPKD kidney, as reported by F. E. Cuppage, R. A. Huseman, A. Chapman, J. J. Grantham in *Kidney Int.* 17:372–81 (1980) and by S. K. Katz, A. Hakki, A. S. Miller, F. S. D., in *Ann. Clin. Lab. Sci.* 19:352–359 (1989). Prominent interdigitating cell processes can also be seen between adjacent cells.

The basement membrane observed in the cysts derived from the human ADPKD system is not readily detectable in the cysts that are produced in the murine CPK model system. This is reflective of the much less prominent basement membrane present in the murine CPK kidney relative to the human ADPKD kidney in vivo.

In the in vitro culture system of the present invention, most of the dispersed human polycystic cells aggregate into clusters of fifty to one hundred cells within four hours. After one day, microscopic lumens can be seen in the clusters of cells that are formed by the polycystic kidney cells. The lumens gradually enlarge and reach a steady state size of 50–200 microns in diameter by day seven.

Although the cultured cells of the murine system of Example 1 contained a heterogeneous population of kidney cells, the cells of the cyst lining showed morphological characteristics of epithelial cells, namely the presence of polarized microvilli and tight junctions. In the CPK mouse, proximal tubules represent the major site of renal cyst formation at the time of birth, but over the next four weeks the proportion of proximal cysts falls and a majority of the collecting tubules in the distal nephron become cystic. The data presented in Table I demonstrate that increased cyst formation, as assayed after 24 hours in culture, correlated with increasing age of the CPK donor. This finding, together with the observed presence of short microvilli on the cells of the cysts leads me to believe the cyst-forming cells are derived from the distal nephron. Suspension cultures of the renal medulla of normal age matched mice did not form in vitro cysts. Thus, I do not believe that this effect was simply dependent on the CPK culture being predominantly composed of collecting duct derivatives.

In contrast to the structures associated with the cysts of the in vitro cpk system, the occasional cell aggregations that formed in suspension cultures of normal mouse kidney cells had a different appearance. These latter aggregates contained a central area of cell debris. There was never evidence for the formation of hollow, spherical cysts that were common in the cultures of the cpk cells.

The LLC-$PK_1$ subline and MDCK cells, which have proximal and distal tubular morphological and biochemical characteristics, respectively, form cysts in suspension culture. When these cell lines are grown in serum-supplemented media, the cyst polarity is apical-side outermost, in common with the current CPK model. However, upon addition of type I collagen as a substratum, the polarity of the cysts from these renal cell lines reverses to mimic the conformation seen in renal epithelia in vivo. In the presence of drugs that elevate intracellular cAMP levels, cysts form in collagen matrices from primary cells derived from both normal human and ADPKD kidneys. However, in the assay system of Example 1, the absence of lumen formation by kidney cells of healthy CPK littermates indicates a fundamental difference of in vitro behavior between cells derived from normal and CPK mouse kidneys.

Previous reports have emphasized the presence of abnormal growth by epithelial cells in murine CPK kidneys. Specifically, histological studies have demonstrated an increased mitotic index in both proximal and distal tubular cells in vivo, and have identified epithelial cell hyperplasia in similar preparations. In addition, abnormal expression of growth-related genes have been found in kidneys of CPK mice: these include the c-myc, c-fos and c-Ki-ras proto-oncogenes and the epidermal growth factor (EGF) gene. In view of the potential importance of abnormal growth in the etiology of in vivo CPK cysts, I performed a series of in vitro studies of cell growth, as assessed by $^3$H-dThd incorporation, in the dispersed cells of the CPK kidneys. I found that growth was exaggerated in CPK cells derived from 21 and 28 day postnatal kidneys compared to age matched healthy controls. In accordance with previous studies of monolayer cultures of CPK kidney cells, I found that suspension cultures of cells from day 10 CPK and age matched normal kidneys showed similar growth rates. Yet, at 10 days after birth, actively dividing cells from phenotypically normal littermates did not form cysts suggesting increased mitosis alone is not sufficient to induce cyst formation in vitro.

Moreover, the addition of cytosine arabinoside effectively abolished $^3$H-dThd incorporation in cultures from CPK kidneys, yet cyst formation was not impaired after 24 hours of culture. These observations therefore dissociate in vitro lumen formation from cell growth. However, these observations do not rule out a permissive role for cell growth in tubular cyst enlargement in the whole organ.

In contrast to the behavior of polycystic human kidney cells in the in vitro system of the present invention, similarly prepared normal human kidney cells rarely aggregated into clusters of more than 10–15 cells. This unique ability of primary cells from polycystic kidneys to form cysts in vitro indicates that these cells express intrinsic morphogenetic information that is different from that expressed by their normal counterparts. Similar observations can be made using the murine CPK cell model. As such, both murine CPK cells and ADPDK cells cultured in accordance with the in vitro methods of the present invention are believed to closely resemble the in vivo disease processes that result in cyst formation. Thus, the use of human ADPDK or murine CPK cells in the in vitro system of the present invention provides unexpectedly superior results in testing therapeutic interventions for cystic diseases in mammals, including humans. A further advantage of the in vitro assay of renal cyst formation of the present invention is that the process is isolated from the confounding effects of glomerular filtration and uremia found in vivo.

Identification of Effective Cyst-Inhibiting Agents

I used the in vitro cyst formation system of the present invention to analyze compounds that affect the process of cyst formation. To determine the therapeutic effectiveness of an agent, cyst-forming cells are suspended in a medium to which the agent has been added. These cells are then cultured on a solid phase without formation of a layer of cells on the surface, such as in the assay system described in Example 1. The extent to which the cells actually form cysts can be detected and compared to the extent of cyst formation expected if no agent were added. If the amount of cyst formation is lower than expected, then the agent is a good candidate for therapeutic intervention of cystic diseases.

Often, the detected level in the presence of the agent is the complete or near-complete absence of cysts. In such cases, the comparison can be entirely qualitative because the expected level of cyst formation is a much higher level of cyst formation. Thus, in these circumstances, the absence of cysts can serve to indicate therapeutic effectiveness for an agent. However, where inhibition is less complete, a control assay should be run in which no agent is added to determine the expected level of cyst formation. The comparison can then comprise a comparison of number and/or size of the resulting cysts.

Agents having known inhibition properties can be added to the assay system in order to elucidate which processes are important to cyst formation. Thus, I tested inhibitors of a variety of processes in my in vitro assay system to determine which of these agents influenced cyst formation. Example 5 provides assays of a variety of metabolic inhibitors on cyst formation using the murine CPK assay model of Example 1.

EXAMPLE 5

In vitro Effects of Compounds

The effects of various metabolic inhibitors on cyst formation were studied in cultures derived from day 21 postnatal CPK mice. The single concentration of each compound, added at the time of cell suspension, was based on values shown previously to inhibit cellular processes in renal epithelial cells. Taxol (25 $\mu$M), a microtubule specific inhibitor, was from Calbiochem (La Jolla, Calif.). All other chemicals were obtained from Sigma Chemical Co. Cytosine arabinoside was added at the final concentration of 20 $\mu$g/ml to inhibit DNA synthesis; $\alpha$-amanitin at 100 ng/ml to inhibit RNA synthesis; cycloheximide at 40 $\mu$g/ml to inhibit protein synthesis; amiloride at 1 mM to inhibit the renal epithelial $Na^+$-$H^+$ exchange; ouabain at 0.5 mM to inhibit $Na^+$-$K^+$-ATPase; brefeldin-A at 10 $\mu$g/ml to inhibit transport of surface proteins; griseofulvin at 350 $\mu$M to inhibit microtubule function; colchicine at 10 $\mu$M to inhibit microtubule polymerization; and cytochalasin-B and cytochalasin-D at 10 $\mu$M to depolymerize actin filaments. At the concentrations used for all of these inhibitors, cell viability was >95% at 24 hours of suspension culture, as assessed by the trypan blue exclusion method. Preliminary data had shown that 1.0 mM ouabain caused extensive cell death.

In the presence of these metabolic inhibitors in vitro, cyst formation was noted to be either present or absent; if present, the diameters of 20 cysts from a 0.2 ml aliquot were measured. In the same samples, $^3$H-dThd incorporation was also measured as described above. In experiments where cyst formation was inhibited, cell clusters were transferred to 15 ml sterile centrifuge tubes (Corning) and washed twice with 10 mls of growth media. After each wash, cell clusters were collected by centrifuging at 200×g for 1 minute and the supernatant discarded. Washed cell clusters were resuspended in the original volume of growth medium without inhibitors, placed in agarose coated wells and incubated at 37° C. in a moisture saturated incubator in 5% $CO_2$ and air.

The effect of metabolic inhibitors on cyst formation and size using the methods of Example 5 are shown in Table II. In this table, the mean cyst size is reported as ±SD with a measurement of twenty cysts. The $^3$H-dThd incorporation is reported as ±SD using measurements of three wells. The * indicates p<0.5 versus control. The § indicates that the cells aggregated into sheets rather than clusters in the presence of these inhibitors. The entries listed as "NA" in the table indicate data that is not available.

TABLE II

Effect of Inhibitors on Cyst Formation of Murine CPK Cells

| Inhibitor | Final Concentration | Cyst Formation (+/−) | Cyst Size ($\mu$m) | $^3$H-dThd Incorporation (% control) |
|---|---|---|---|---|
| Control | — | + | 71 ± 22 | 100 ± 11 |
| Cytosine arabinoside | 20 $\mu$g/ml | + |  | 70 ± 21*2 ± 2 |
| $\alpha$-amanitin | 100 ng/ml | + | 65 ± 27 | 71 ± 10 |
| Cycloheximide | 49 $\mu$g/ml | + | 68 ± 17 | 88 ± 20 |
| Ouabain | 1 mM | − | 0 | 104 ± 9 |
| Amiloride | 1 mM | − | 0 | 72 ± 25 |

TABLE II-continued

Effect of Inhibitors on Cyst Formation of Murine CPK Cells

| Inhibitor | Final Concentration | Cyst Formation (+/−) | Cyst Size ($\mu$m) | $^3$H-dThd Incorporation (% control) |
|---|---|---|---|---|
| Brefeldin-A | 10 $\mu$g/ml | − | 0 | NA |
| Griseofulvin | 350 $\mu$M | − | 0 | NA |
| Colchicine | 10 $\mu$M | − | 0 | 97 ± 12 |
| Vinblastine | 1 $\mu$M | − | 0 | 93 ± 9 |
| Nocodazole | 30 $\mu$M | − | 0 | 87 ± 16 |
| Taxol | 25 $\mu$M | − | 0 | 90 ± 11 |
| Cytochalasin-B | 10 $\mu$M | − | $^\S$0 | 96 ± 5 |
| Cytochalasin-D | 10 $\mu$M | − | $^\S$0 | 97 ± 2 |

As discussed above, the data in Table II are derived from experiments in murine CPK cells. Murine cells are relatively resistant to ouabain, and thus, ouabain was found not to inhibit cyst formation in these cells. However, at higher ouabain concentrations (1 mM) cyst inhibiting activity was observed. When similar experiments were conducted using human ADPKD cells, ouabain was found to be a potent inhibitor of cyst formation. The CPK gene defect is not believed to be exactly analogous to the ADPDK gene defect. Thus, some differences between effects are to be expected. However, certain features of cyst formation appear to be constant across species and disease state. For example, all of the inhibitors tested to date that affect cytoskeletal components inhibit cyst formation in both the murine and human models. One particularly preferred class of compounds for use in the present invention is taxol and derivatives thereof. A variety of such derivatives can be made in accordance with methods well known in the art. Other inhibitors of microtubules, such as colchicine, nocodazole, vincristine and vinblastine are also effective when used in accordance with the present invention. Inhibitors of actin, such as cytochalasin-B and cytochalasin-D are also effective in preventing cyst formation. In addition, inhibitors of membrane protein transport, such as brefeldin A can also be used in accordance with the present invention.

Neither cytosine arabinoside (20 $\mu$g/ml), α-amanitin (100 ng/ml) nor cycloheximide (40 $\mu$g/ml) inhibited cyst formation in the human ADPKD system. These results indicate that DNA, mRNA and protein synthesis, respectively, are not required for ADPKD cyst formation in vitro.

Of the inhibitors of DNA, RNA and protein synthesis, only α-amanitin caused a small, but significant, decrease in $^3$H-dThd incorporation. In contrast, cytosine arabinoside (20 mg/ml) produced a profound decrease in $^3$H-dThd incorporation to 2±2% of control values, but cyst formation was not affected and the mean cyst diameter was similar to the control value.

The ability of both types of polycystic renal cells to form cysts in vitro in the absence of DNA synthesis suggests that cellular hyperplasia is neither a primary nor a causal factor in this model of cyst formation but is only necessary for the continual enlargement of cysts.

In organ culture of neonatal CPK kidneys proximal tubular cysts regress spontaneously, but can be maintained by pharmacological doses of triiodothyronine. This effect is abolished by the addition of 0.2 mM ouabain: these maneuvers increase and decrease renal Na$^+$K$^+$-ATPase activity, respectively. This enzyme, which is located on the basolateral surface of normal renal epithelia in vivo, provides the major driving force for solute transport out of the tubule lumen, and histological studies of both CPK and ADPKD kidneys have demonstrated mislocalization of this enzyme to the apical membrane. We thus investigated the effect of ouabain on the CPK in vitro system. At a concentration of 0.5 mM ouabain did not prevent the formation of CPK cysts after 24 hours of suspension culture, but this dose is not always sufficient to completely block murine Na$^+$-K$^+$-ATPase. A higher dose (1.0 mM) resulted in a large scale reduction of cell viability in our culture system.

Amiloride (1 mM), or ouabain (0.5 mM) completely block cyst formation when human ADPKD cells are used in the model. Sodium and proton transports are the principal driving forces responsible for the trans-epithelial movement of water in kidney tubules. Inhibition of cyst formation by amiloride and ouabain in the human model indicate that they play important roles in fluid accumulation within cysts. The inhibition of cyst formation by ouabain and amiloride is reversible; lumens begin to appear in cell aggregates twenty-four hours after removing the inhibitors.

Inhibitors of microtubules, such as taxol (25 $\mu$M), coichicine (10 $\mu$M), and vinblastine (1 $\mu$M), all reversibly inhibited in vitro cyst formation in both models. These results suggest that functional microtubules are required for cysts to form. The exact mechanisms by which these compounds inhibit cyst formation is not certain. I believe that inhibitors of microtuble functions can be blocking cyst formation by inhibiting the clustered cells from developing a polarized phenotype, or the targeted delivery of cellular proteins necessary for maintaining cellular polarity. It is also possible that some other heretofore unknown mechanism exists.

Both cytochalasin-B (10 $\mu$M) and cytochalasin-D (10 $\mu$M) effectively inhibited cyst formation in both models. These drugs inhibit the formation of the actin microfilament component of the cytoskeleton. When either of these agents were added at the onset of the in vitro cyst formation experiments, dispersed cells aggregated but lumens were not observed during the 24 hour observation period. At the concentration used, these compounds exhibited insignificant effects on DNA synthesis, reported as $^3$H-dThd incorporation in Table II. When the cytochalasins were added to the murine cyst formation assay, cells clustered into flat sheets of about 50 rounded cells. Removal of the cytochalasins after 24 hours did not result in cyst formation in this model. On the contrary, the inhibitory effects of all of the microtubule specific agents were reversible, as after 24 hours of inhibitor treatment, lumens developed within cell clusters 4–5 hrs after clustered cells were washed and resuspended in growth medium without inhibitors.

I also tested the anti-viral drug, Brefeldin A. This drug inhibits the delivery of membrane proteins to the membrane of cells. Brefelden A completely inhibited cyst formation in my in vitro model. Transport of vesicles usually is along microtubules. Thus, it is possible that the mode of inhibition of cyst formation for drugs that inhibit delivery of membrane proteins to the membrane is the same mode of action as for agents that affect the cytoskeleton. However, other possible modes of action exist, and I do not desire to be bound by any particular mode of action.

The most striking finding among the various metabolic inhibitors which we have tested regard the compounds which specifically interfere with cytoskeletal assembly and functions. Cyst formation can be reversibly inhibited by any of colchicine, vinblastine, nocodazole or taxol in both murine and human in vitro models. These results indicate that cytoskeletal function, including microtubule and microfilament function, is necessary for the formation of cysts. Agents that affect transport of membrane proteins to the membrane also affect cyst formation in vitro.

Drugs Useful in the In Vivo Treatment of Cysts

Through the use of the foregoing inventive method of screening for drugs and other agents that are useful in the treatment of cysts, I discovered that agents which interfere with the normal functioning of cytoskeletal components are useful in both the in vitro and in vivo treatment of cysts. Cyst formation can be reversibly inhibited by either colchicine, vinblastine, nocodazole, taxol or derivatives thereof. All of these are agents that affect the normal functioning of microtubules and microtubule components in a cell. Thus, it is believed that other such agents will provide similarly therapeutic effects. Cyst formation can also be treated with agents that affect the microfilament network of a cell, usually by acting on the main component of microfilaments, actin. Cytochalasin B, cytochalasin D and phalloidin are examples of such agents. Other agents which affect cyst formation include a drug which interferes with the transport of membrane proteins to the cell membrane, brefeldin A.

Derivatives of taxol have been made in order to produce more effective chemotherapeutic agents for cancer. I believe that some of these derivatives will prove especially effective in connection with the methods of the present invention. Additional derivatives can be made and tested for cyst-treating activity in accordance with the methods described herein or by methods well known to those having ordinary skill in the art.

The mode of action of those agents which specifically act on microtubules is well defined. Microtubules comprise one of the major components of the cytoskeleton and consist of polarized, dynamically maintained tubular structures consisting of ordered filamentous polymers of α-tubulin/β-tubulin heterodimers. The two ends of a microtubule exhibit different rates of addition of tubulin dimers and act as the growing (plus) and the vanishing (minus) end respectively. Colchicine and nocodazole both bind stoichiometrically to the same site or the dimeric form of a tubulin heterodimer and subsequent binding of the tubulin-colchicine complex to either end of a microtubule effectively caps the microtubule at the growing end thereof. Since disassembly continues at the opposite end of the microtubule, the capped microtubule rapidly disassembles in the presence of colchicine.

Binding of vinblastine to tubulin induces the formation of paracrystalline aggregates of free tubulin in a cell. The formation of such aggregates prevents the polymerization of tubulins into microtubules. Therefore, in the presence of vinblastine, preformed microtubules rapidly depolymerize.

In contrast to the foregoing agents which inhibit cyst formation by causing microtubules to disassemble, taxol inhibits microtubule disassembly. Taxol, in fact, stabilizes microtubules and promotes microtubule assembly from free tubulin. By preventing the normal disassembly of microtubules, taxol interferes with microtubule functions without disrupting the cytoskeleton.

All of these anti-microtubule agents are antimitotic because they interfere with the functions of microtubule-based mitotic spindles. However, their ability to prevent cyst formation is clearly not related to their antimitotic activity. When DNA synthesis is completely blocked by cytosine arabinoside in cyst-forming cells such as kidney cells from humans with polycystic kidney disease, no effect on in vitro cyst formation is observed.

In interphase cells, microtubules have several diverse important physiological functions. As a major component of the cytoskeleton, microtubules contribute to the maintenance of the cellular architecture. In living cells the endoplasmic reticulum extends and retracts processes, forming and dissolving a tubular network along the microtubule cytoskeleton. Depolymerization of the microtubules by nocodazole collapses the endoplasmic reticulum membranes into the nuclear region. The same treatment causes fragmentation and dispersal of the Golgi apparatus from the nuclear region. Upon removal of nocodazole, the Golgi fragments reassemble in the juxtanuclear region.

In addition to providing structural support, microtubules participate in many aspect of membrane vesicles mobility within the cell. For example, in exocytosis, membrane vesicles leave the Golgi carrying newly synthesized proteins to the cell surface along microtubule tracks. In endocytosis, vesicles travel via microtubule-based movement to the cell center where fusion with prelysosomal compartments occurs. Depolymerization of microtubules with nocodazole inhibits this process. The movement of intermediate vesicles between the endoplasmic reticulum and the Golgi apparatus has also been shown to occur along microtubules.

Although the mode of action of brefeldin A has not yet been characterized, it has been observed that this drug blocks the movement of membrane proteins between the endoplasmic reticulum and the Golgi bodies. It is postulated that this agent also affects cyst formation by acting on processes that are microtubule-dependent or dependent on other components of the cytoskeleton. The transport of membrane proteins usually takes place by means of vesicles which are moved along microtubules. One reason for this blockage of movement could be due to some interference with the microtubules along which such vesicles are transported.

Microtubules have also been found to play important roles in the biogenesis and maintenance of epithelial cell polarity. During early development of the mouse embryo, formation of the first polarized epithelium is represented by the formation of the trophectoderm from blastomeres in a process known as compaction. Nocodazole allows the development of surface polarity but inhibits the formation of cytoplasmic poles during compaction, while taxol has the opposite effect. After polarity is established, the functional polarity of epithelial cells is maintained by targeted delivery of the respective secreted and membrane proteins to their proper destinations. The mechanisms that direct this sorting process are not well characterized; however, microtubules are clearly involved. If microtubules are depolymerized, both secreted and membrane proteins that normally are delivered apically or basolaterally are still synthesized but are mostly delivered in an undirected fashion.

Another proposed basis for the efficacy of agents which affect the cytoskeleton in treating cysts is that such agents, in addition to interfering with the normal functioning of cytoskeletal components, also interfere with the mechanisms or structures that establish or maintain the polarity of a cell. Cysts exhibit a definite polarity, which can be seen in that cyst cells transport solutes such as sodium and hydrogen ions into the lumen of the cyst, thereby creating an intraluminal pressure greater than the pressure outside the cyst. Thus, in a culture of human polycystic kidney cells, cyst formation can be blocked by the addition of 1 mM amiloride or 0.5 mM ouabain, which block hydrogen ion and sodium ion transport, respectively. Conceivably, the agents that interfere with the cytoskeleton exert their effects by influencing the polarity of the cell. This could result from disrupting polarity (in the case of nocadazole) or by preventing a change in the polarity of the cell (in the case of taxol).

Treatment of Cysts In Vivo

One of the surprising discoveries of the present invention is that drugs affecting the cytoskeleton of a cell, such as those which have been identified through the foregoing inventive screening method, can be used to treat cystic diseases in vivo. It has been demonstrated that such drugs can extend the lives of CPK mice. Subjects who suffer from a variety of cystic diseases, including the similar Polycystic Kidney Disease in humans are also believed treatable.

A. Treatment of Murine Cysts In Vivo

One of readily available and reproducible animal models of renal cyst formation is the cpk/cpk (CPK) mouse which arose as a spontaneous mutation of the C57BL/6J strain housed at the Jackson Laboratories (Bar Harbor, Me.). The homozygous recessive pups are born with mild distention of the proximal renal tubules. Within a month the kidneys of these mice become grossly enlarged as the result of marked cystic dilatation of the renal collecting ducts. Finally, death from uremia occurs in the fourth postnatal week. Given this clinical course, the murine defect resembles human autosomal recessive polycystic kidney disease, a disorder which is a common cause of childhood renal failure.

I believe that the use of agents that affect the cytoskeleton or that affect the transport of membrane proteins in a cell can inhibit formation of a large number of renal and other cysts in mice. The diseases associated with such cysts can thereby be treated. One such agent which has been found to be particularly effective is the anti-cancer drug, taxol. In one study, 15 $\mu$l of taxol (10 mg/ml in DMSO, a sub-lethal dose) was administered once intraperitoneally to CPK homozygous mice approximately 10–12 days after their birth. Other such mice were either untreated or were treated once with 15 $\mu$l DMSO administered intraperitoneally. Mice that were untreated or treated only with DMSO survived only 25–28 days, as would be expected for homozygous CPK mice. Those treated with a single administration of taxol survived an additional 12 and 19 days.

In order to determine whether taxol prevents cyst formation by inhibiting cell division, another drug known to have anti-mitotic activity, methotrexate, was tested for its ability to treat homozygous cpk mice. Six cpk mice were injected intraperitoneally with 15 $\mu$l of methotrexate solution (1.1 mg/ml in water) 10–12 days after birth and once every week thereafter. The methotrexate-injected mice survived until between 18 and 27 days after birth, with only one mouse living longer than 28 days. Thus, the methotrexate treated mice did not appear to survive substantially longer than untreated controls. Therefore, the anti-mitotic activity of taxol cannot explain its ability to treat CPK mice having a polycystic-type kidney disease. Rather, the results from in vitro tests indicate that agents which interfere with the function of the cytoskeleton, or which inhibit the delivery of membrane proteins are useful in treating cystic diseases such as Polycystic Kidney Disease.

EXAMPLE 6

Treatment of CPK Mice with Taxol

Mice were obtained from the Jackson Laboratories (Bar Harbor, Me.). Homozygous CPK mice were identified by the presence of intra-abdominal distention, palpable at 10 days after birth, and visible in the third and fourth weeks of life. Heterozygous mice, which have a normal kidney phenotype, were identified by the presence of polycystic offspring and were bred to provide the litters used in this study. Animals were kept on a 12 hour light/dark cycle and received Purina Mouse Chow and water ad libitum.

When every newborn mouse in a litter attained a body weight of more than 5.5 gm, ie. between ten to twelve days of age, each offspring of heterozygous CPK mice (C57BL/6J-cpk/+) was given 15 $\mu$l of taxol (10 mg/ml in DMSO) or 15 $\mu$l DMSO alone intraperitoneally. All juvenile animals were kept with their mother, weighed every other day, and weaned when they were 25 days old. The presence of bilaterally enlarged polycystic kidneys was determined by palpating affected animals weighing 5.5 grams or more. As a result of this treatment, the untreated homozygous CPK mice and those treated with DMSO alone survived until day 25–28 postnatal, while those treated once with taxol survived at least 12–19 days longer.

The drug taxol prevents the depolymerization of microtubules and thus prevents the proper operation of the microtubule-based mitotic spindles involved in cell division. The anti-cancer effect of taxol is based on its ability to inhibit cell division.

Examples 7 and 8 are provided to show further evidence of the effectiveness of taxol in the in vivo treatment of cysts.

EXAMPLE 7

The Effect of Taxol and Methotrexate in Treating Murine Renal Cysts

Homozygous CPK mice, raised and identified as in Example 6 were treated with either 15 $\mu$l of taxol (10 mg/ml in DMSO), 15 ul of methotrexate (1.1 mg/ml in saline), or 15 $\mu$l DMSC alone intraperitoneally at 10 to 12 days postnatal. Those mice treated with DMSO alone or with methotrexate died approximately 25 to 28 days postnatal, while those treated once with taxol survived 12–19 days longer.

Thus, Examples 6 and 7 demonstrate that even a single dose of taxol can provide some in vivo therapeutic effect. Example 8 shows the results with repeated administrations of taxol Since taxol is eventually metabolized by mammals, having an in vivo half-life approximately 6–12 hours in humans, a further experiment was conducted in which periodic administrations of taxol were given to homozygous CPK mice. This study is shown below in Example 8.

EXAMPLE 8

Effect of Weekly Taxol or Methotrexate on cpk Mice

Eleven homozygous cpk mice, raised and identified as in Example 6 were treated with 15 $\mu$l of 10 mg/ml taxol in DMSO through intraperitoneal injection beginning 11–14 days after birth. Following the first treatment, the mice were administered with the same treatment once every week thereafter. As controls, 6 cpk mice were treated with 15 $\mu$l intraperitoneal injections of DMSO beginning 10–12 days after birth and then once every week thereafter.

Figure 1A:
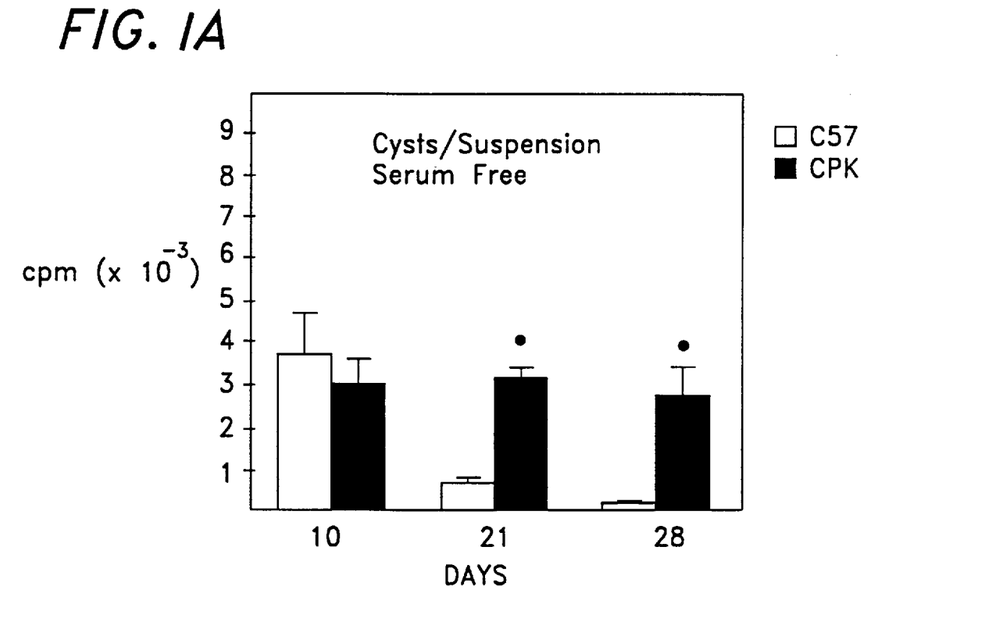
Figure 1B:
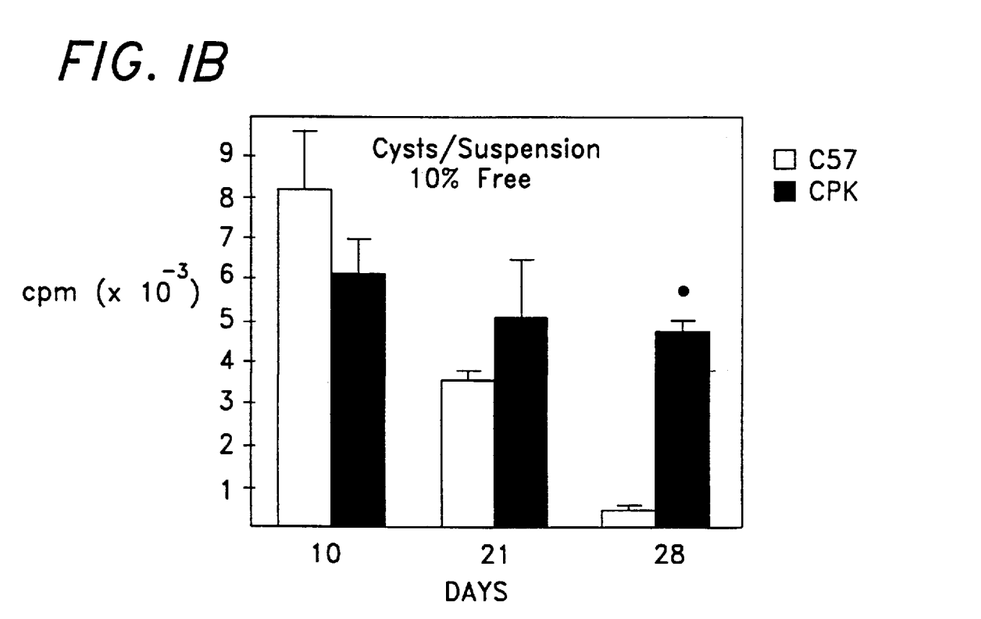
Figure 1C:
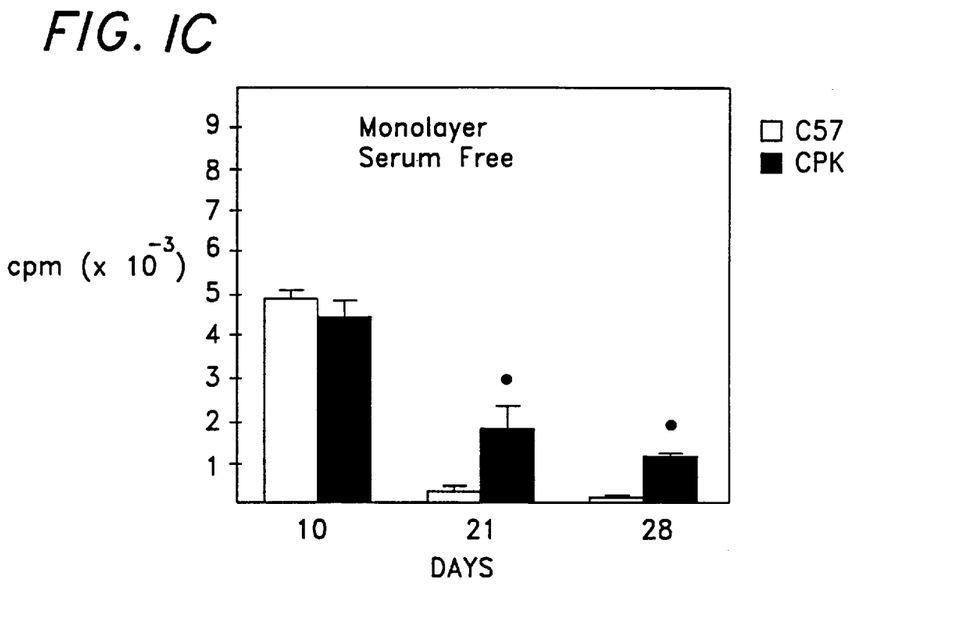
Figure 1D:
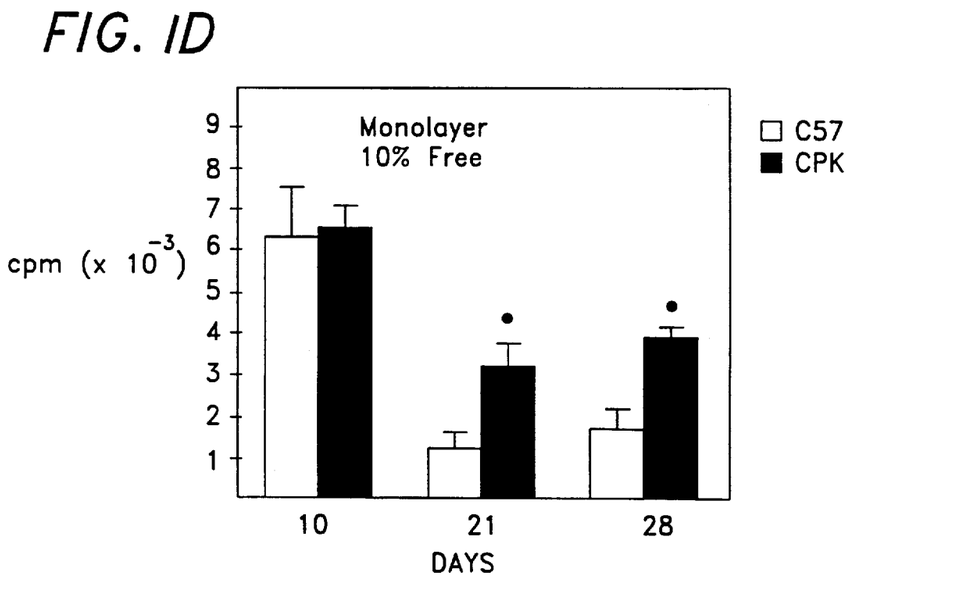
Figure 2:
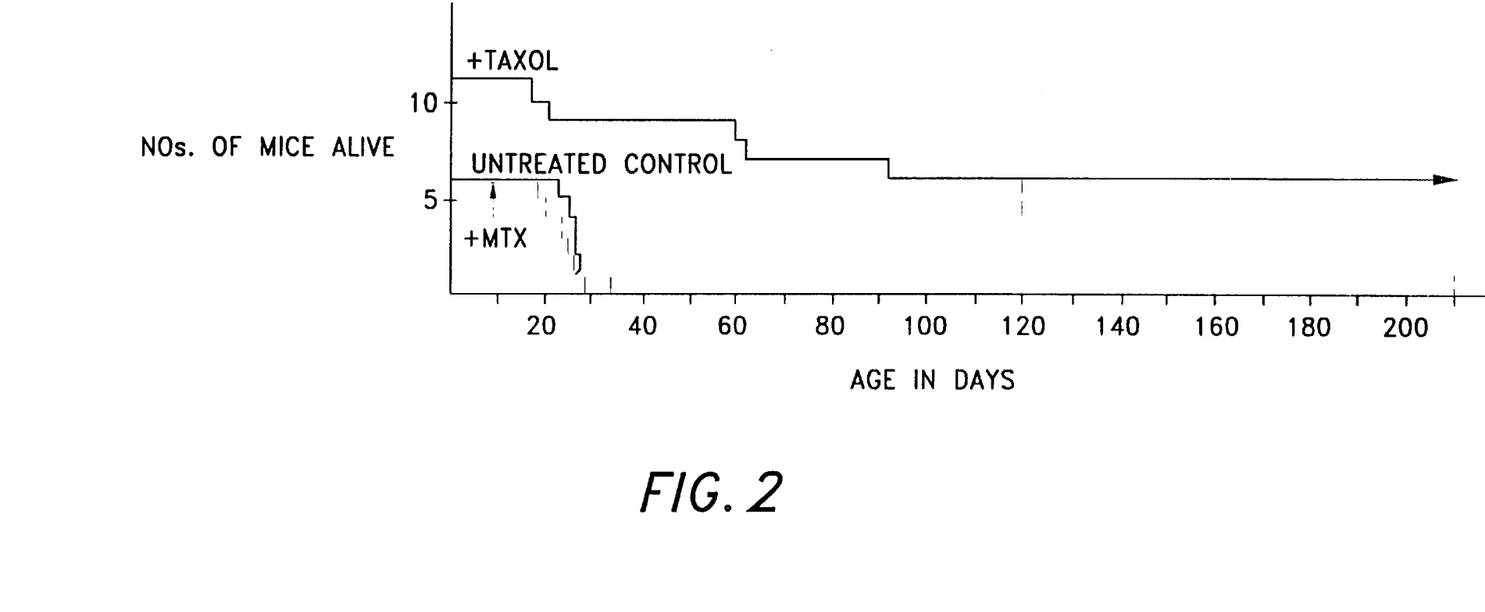
FIG. 2 shows a graph of the effects of weekly taxol or methotrexate treatment on the survival of polycystic cpk mice. Untreated and methotrexate (MTX) treated polycystic cpk mice all died before 30 days of age. Most polycystic cpk mice treated with weekly taxol survive more than 60 days. The dotted line starting at day 120 indicates the number and age of apparently healthy taxol treated polycystic mice that were sacrificed for histology studies. Pairs of mice were sacrificed at 120 days, 182 days and 210 days of age. These mice all remained active until sacrifice and attained adult size and weight, despite having palpably enlarged kidneys.

The results of this therapeutic regimen are shown in FIG. 2. The mice injected with DMSO alone survived 24–28 days following birth. The mice injected weekly with taxot, however, generally experienced substantially longer life spans. Although two died before the first DMSO-injected mouse, the remaining six mice lived more than 120 days. The two taxol-injected mice that died before 30 days of age are believed to have received an overdose of taxol.

Histological examination of kidney sections from taxol-treated cpk mice demonstrated the presence of many normal glomeruli and many normal to slightly dilated renal tubules in both the kidney cortex and medulla. The cysts observed in the polycystic kidneys of cpk mice that were treated with taxol for as long as 210 days after birth were both less numerous and less dilated than the cysts that were found in 21-day old untreated polycystic kidneys. The fact that normal tubules were almost completely absent in end-stage cpk kidneys, but were clearly apparent in the kidneys of 210 day old taxol-treated cpk mice suggests that the collecting duct cyst formation and the expansion phase of the disease had been arrested or retarded. The kidney damage that I did observe in taxol-treated cpk mice was not likely due to the taxol treatment itself since control mice treated for 200 days with weakly doses of taxol exhibited a normal kidney histology.

Figure 3A:
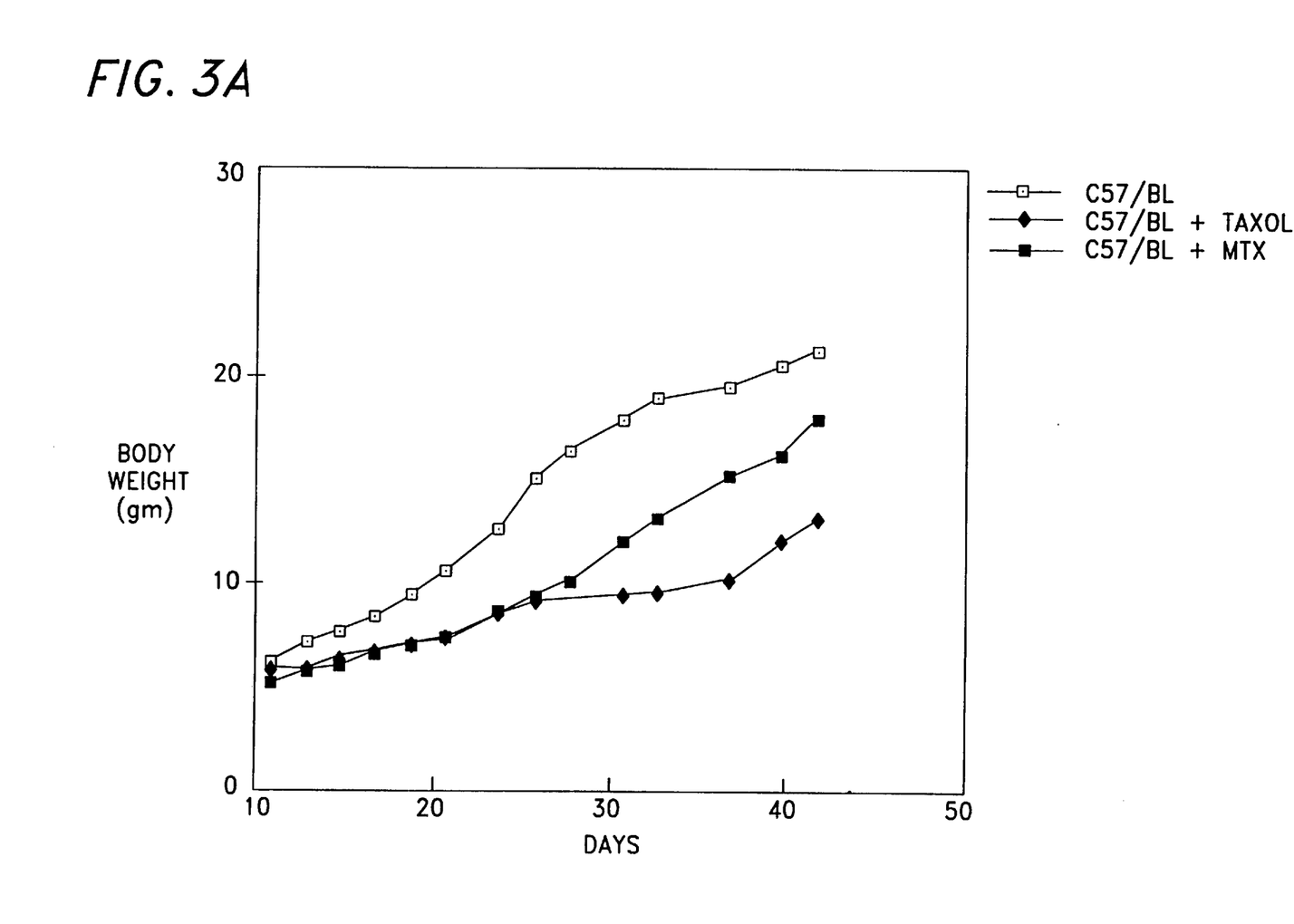
Figure 3B:
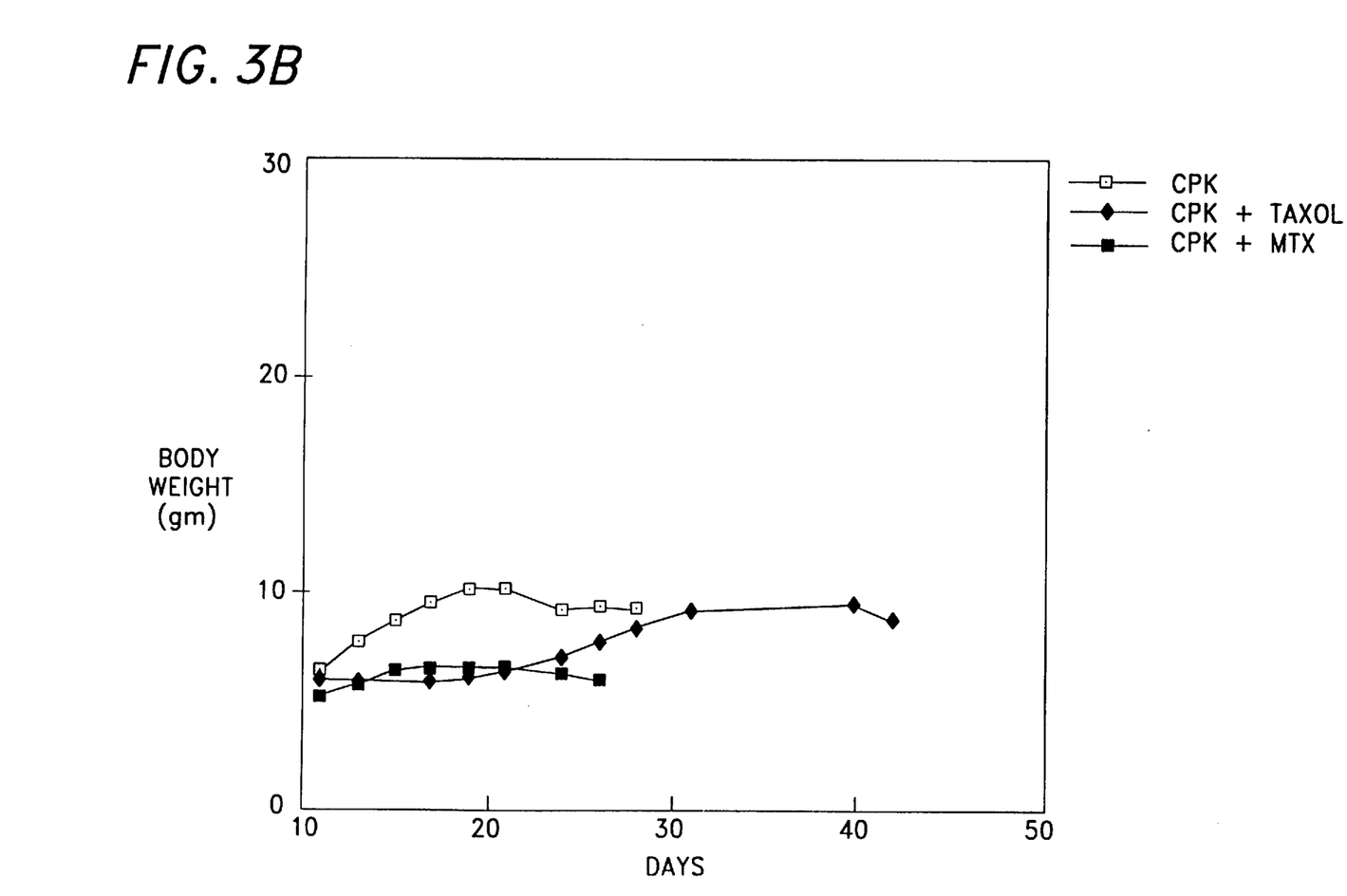

In a related procedure I treated both normal C57BL/6 and cpk mice at 11–14 days of age with either taxol or methotrexate as described above. Six untreated mice served as controls in this experiment. The results of this procedure are shown in FIG. 3B. Clearly, the taxol treated mice experienced substantially longer lifespans than either the DMSO or methotrexate-treated mice. The longer life span did not appear to result from extrinsic factors such as increased weight gain because the taxol-treated mice gained weight at substantially the same or lower rate than the DMSO or methotrexate treated mice. FIG. 3A shows results of weight measurement experiments for normal phenotype, heterozygous mice. For these mice, the taxol-treated group gained less weight than the methotrexate or non-treated groups. Thus, it does not appear that the increased life span of the taxol treated CPK mice was secondary to increased weight gain.

Example 9 provides a further demonstration that chemical agents which block in vitro cyst formation also can extend the lifespans of animals that ordinarily succumb to cystic disease. The results presented in Table II indicate that griseofulvin inhibits the formation of cysts in the in vitro cpk model of PKD. Although the mechanism of its inhibitory activity is not presently understood, this antifungal agent is known to have a colchicine-like effect on mitosis. Example 9 presents the results of a weekly treatment protocol in which young cpk mice were administered with griseofulvin. These results are considered as preliminary only because the test animals continue to survive as of this report. For this reason, the value given below for the average lifespan of cpk mice treated with griseofulvin represents a minimal value. This value increases with every day the remaining animals in this trial continue to survive.

EXAMPLE 9

Treatment of cpk Mice with Griseofulvin

Nine homozygous cpk mice, raised and identified as in Example 6 were treated with 25 $\mu$l of 24 mg/ml griseofulvin in DMSO through intraperitoneal injection beginning 10–12 days after birth. After the first treatment, the mice were administered with the same treatment once every week thereafter. Six of the mice have died so far. These deaths occurred at 31, 34, 35, 41, 45 and 60 days of age. The remaining mice are still alive at 54, 63 and 78 days of age. Given these results, it is possible to conclude that the minimum average lifespan of the mice that received periodic administration of griseofulvin in this trial is at least 49±15.8 days. Thirteen untreated control cpk mice that were palpably polycystic before 13 days of age lived 33.5±6.3 days.

B. Treatment of Human Cysts In Vivo

Cysts such as those formed in the kidney of a patient with Polycystic Kidney Disease can also be treated in human subjects. In order to treat such cysts, a subject having a cystic disease or at risk for developing a cystic disease is first identified. For example, a subject can be identified by a physician, who diagnoses that subject as having Autosomal Dominant Polycystic Kidney Disease. Such a subject is then a candidate for undergoing the present treatment for cystic diseases.

After identifying an appropriate subject for treatment, that subject is administered a pharmaceutically effective dose of a compound or agent which interferes with the functioning of the cytoskeletal components of cells, or an agent which interferes with the transport of proteins to cell membranes. Such a compound can be administered either before a cyst has formed, in order to prevent its formation, or after a cyst has already been detected in a subject. Preferably, especially where the compound is one that is metabolized by the subject, the compound is administered periodically during the time the patient has or is susceptible to developing a cyst. In this way an effective amount of the compound can be maintained in the subject.

One agent that affects the functioning of the cytoskeleton which has been identified as being useful in the practice of the present invention is taxol. Taxol can be administered in a variety of ways, including intravenously, intraperitoneally, intramuscularly, or in any other appropriate way known to the art. A dose of taxol can be administered in the range of 0.01 to 500 mg, preferably in the range of 10 to 250 mg/m$^2$ of body surface area (bsa), depending on the method of administration. For example, 250 mg of taxol can be infused intravenously into a subject over a 24 hour period in DMSO. This treatment can be repeated every 21 days. Alternatively, about 100 mg of taxol in an appropriate pharmaceutical carrier can be injected intravenously every week into an adult subject. Example 10 is provided to illustrate one exemplary method of treating a human being having a cystic disease.

EXAMPLE 10

Treatment of Polycystic Kidney Disease in Humans

A human subject is diagnosed as having Autosomal Dominant Polycystic Kidney Disease by a physician. That subject is injected intravenously with 150 mg/m$^2$ of a water-soluble taxol derivative in approximately 10 ml of saline solution. This treatment is repeated weekly.

Besides taxol, a number of other drugs which affect the cytoskeleton can also be used to treat cysts. These drugs include vinblastine sulfate (vinblastine), vincristine sulfate (vincristine), colchicine and griseofulvin (fulvicin). Vinblastine, sold as Velban (Eli Lilly, Indianapolis, Ind.) can be administered intravenously once per week in an amount between 0.1 and 15 mg/m$^2$ bsa, preferably between 2 and 12 mg/m$^2$ bsa, dissolved in 10 ml saline solution. Vincristine (Eli Lilly, Indianapolis, Ind.) can also be administered intravenously in a glucose or saline solution, in an amount between 0.1 and 5 mg/m$^2$, preferably between 1 and 2.5 mg/m$^2$, weekly. Colchicine (Eli Lilly, Indianapolis, Ind.) can also be administered intravenously in a saline solution weekly in a dosage of between 0.1 to 5 mg, and preferably between 1 and 3 mg, per administration. Griseofulvin, sold as Fulvicin (Schering-Plough, N.J.), can be administered orally in dosages ranging from 125–500 mg daily. Further information regarding these commercially available pharmaceutical preparations can be found in the "Physicians' Desk Reference," published annually by Medical Economics Data of Oradell, New Jersey.

Other drugs in less frequent clinical use than those described above have also been identified as being efficacious in the method of the present invention in treating cystic diseases such as Polycystic Kidney Disease. For example, cytochalasin B or cytochalasin D, which interfere with the polymerization of actin in microfilaments, can be administered to treat cystic diseases. Brefeldin A, a drug which interferes with the transport of proteins to a cell membrane, can also be administered. Those of skill in the art will know how to choose an appropriate pharmaceutical carrier. The carriers, excipients or diluents used in the commercially available products discussed above are appropriate in many instances. Those of skill in the art will also appreciate how to discover an appropriate dosage of such anti-cystic compounds or agents through such routine experiments as conducting animal and human trials.

In addition to the derivatives of taxol discussed above, I also believe that other chemical derivatives of the cytoskeletal inhibitors that are named in this application are effective in the treatment of polycystic disease. For example, I expect that derivatives of brefeldin-A that exhibit long in vivo half-lives would be more effective than brefeldin-A in their ability to inhibit cyst formation. One of ordinary skill in the art will readily appreciate how the methods described herein and detailed in the Examples presented above can be used to test such compounds for their ability to inhibit cyst formation in vitro and in vivo in both the mouse and human experimental systems that are described in this application.

Finally, I believe that cystic diseases other than Polycystic Kidney Disease can also be treated with drugs such as those previously identified. For example, a number of other cystic kidney diseases are believed treatable with these drugs. Such diseases include acquired polycystic kidney disease, juvenile nephronophthisis medullary cystic disease complex, medullary sponge kidney, renal dysplasia, tuberous sclerosis, von Hippel-Lindau Syndrome, solitary multilocular cysts, pyelocalyceal cysts, pericalyceal lymphangiectasis, and hilar and perinephric pseudocysts. Cystic diseases other than those of the kidney can be treated as well, including cysts of the lung, spleen, liver, and ovary.

What is claimed is:

1. A method of producing a culture of cells which form cysts in vitro, comprising:
    preparing a suspension of cells that form cysts in vivo in a medium suitable for the maintenance of said cells; and
    culturing said cells on a solid phase which substantially prevents the formation of a layer of said cells on the surface of said solid phase.

2. The method of claim 1, wherein said solid phase is coated with a material which substantially prevents the growth of a layer of said cells.

3. The method of claim 2, wherein said material is agarose.

4. A culture of cells, wherein said cells are suspended in a medium suitable for the maintenance of said cells in culture, and wherein said cells form cysts in vitro without induction by a cyst-inducing agent.

5. The culture of claim 4, wherein the apical surfaces of said cells face the lumens of said cysts.

6. The culture of claim 4, wherein said cells are of distal nephron origin.

7. The culture of claim 4, wherein said cells are capable of forming cysts within 24 hours of culture.

8. The culture of claim 4, wherein said cells have DNA synthesis capabilities that are greater than normal.

9. The culture of claim 4, wherein cysts formed by a said cell have an outer cell layer from about 1 to 5 cells thick, and about 10 to 50 cells in circumference.

10. The culture of claim 4, wherein cysts formed by said cells have an abnormally thickened basement membrane.

11. The culture of claim 4, wherein cells line said cysts and the cells lining said cysts have prominent interdigitating cell processes therebetween.

12. The culture of claim 4, wherein said cells have short sparse microvilli on the anti-luminal surface.

13. The culture of claim 4, wherein said cells have been produced by a method comprising:
    preparing a suspension of said cells that form cysts in vivo in a medium suitable for the maintenance of said cells; and
    culturing the suspension of cells on a solid phase which substantially prevents the formation of a monolayer of said cells on the surface of said solid phase.

14. The culture of claim 13, wherein said solid phase is coated with a material which substantially prevents the growth of a layer of said cells.

15. The culture of claim 14, wherein said material is agarose.

16. A method of screening an agent in vitro in order to determine the effectiveness of the agent in treating a cystic disorder, comprising:
    forming a suspension of cells which form cysts in vivo in a medium comprising an agent to be tested for its ability to inhibit cyst formation;
    culturing said cells in said medium on a solid phase without formation of a layer of said cells on the surface of said solid phase;
    detecting the extent to which said cells form cysts;
    comparing the result form detecting the extent of cyst formation with the extent of cyst formation when said cells were cultured in a medium without said agent; and
    identifying said agent as effective in treating a cystic disorder if the detected extent of cyst formation is less than the extent of cyst formation in the medium without said agent.

17. The method of claim 16, wherein said agent is a compound that interferes with the normal metabolism of a cytoskeletal component.

18. The method of claim 16, wherein said agent is a compound that inhibits the delivery of membrane proteins to the membrane of said cells.

19. The method of claim 17, wherein said agent is one of the following: taxol, cytochalasin-B, cytochalasin-D, phalloidin or a derivative of any of the foregoing.

20. A method of treating a mammal having a cystic disease, comprising:
    administering to the mammal a pharmacologically effective anti-cystic amount of an agent that interferes with the normal functioning of a cytoskeletal component, said agent being administered in pharmacologically acceptable carrier, excipient or diluent.

21. The method of claim 20, wherein said drug is specific for microtubules.

22. The method of claim 20, wherein said drug is specific for actin microfilaments.

23. The method of claim 21, wherein said drug is selected from the ground consisting of: taxol, colchicine, nocodazole, vincristine, vinblastine, griseofulvin and derivative of any of the foregoing.

24. The method of claim 22, wherein said drug is selected from the group consisting of: cytochalasin-B, cytochalasin-D, phalloidin, phallacidin and a derivative of any of the foregoing.

25. A method of treating a mammal having a cystic disease, comprising:

administering to the mammal a pharmacologically effective anti-cystic amount of an agent that inhibits the delivery of membrane proteins to the membrane of a cell of said mammal, said agent being administered in a pharmacologically acceptable carrier, excipient or diluent.

26. The method of claim 25, wherein said agent comprises brefeldin A.

27. The method of claim 25, wherein said drug is taxol or a derivative thereof.

28. A pharmaceutical composition useful for inhibiting cyst formation in a mammal, comprising:

a cyst-inhibiting amount of taxol; and dimethylsulfoxide as a carrier.

29. The pharmaceutical composition of claim 28, wherein the cyst-inhibiting amount of taxol is an amount ranging from 0.01 to 500 mg.

30. The pharmaceutical composition of claim 28, wherein the mammal has a body surface area, and wherein the cyst-inhibiting amount of taxol is an amount corresponding to from 10 to 250 mg/m$^2$ of said body surface area.

* * * * *